United States Patent [19]

Sherlock et al.

[11] Patent Number: 4,625,734

[45] Date of Patent: Dec. 2, 1986

[54] URINE METER AND DRAINAGE BAG COMBINATION

[75] Inventors: Paul Sherlock, San Francisco, Calif.; Benjamin Brausen, Cromwell, Conn.; Phillip P. Klein, Plano, Tex.

[73] Assignee: Sherwood Medical Company, St. Louis, Mo.

[21] Appl. No.: 638,134

[22] Filed: Aug. 6, 1984

[51] Int. Cl.$^4$ .......................... A61B 5/00; B65D 33/00
[52] U.S. Cl. .................................... 128/762; 128/766; 128/767; 604/323; 604/325
[58] Field of Search .................. 604/317, 324–325, 604/323; 128/760, 762, 766, 767, 771; 73/171

[56] References Cited

U.S. PATENT DOCUMENTS

| Re. 30,607 | 5/1981 | Manschot et al. | 128/762 |
| 3,345,980 | 10/1967 | Coanda | 128/762 |
| 3,661,143 | 5/1972 | Henkin | 128/2 |
| 4,095,589 | 6/1978 | Manschot et al. | 128/762 |
| 4,178,934 | 12/1979 | Forman | 128/762 |

Primary Examiner—C. Fred Rosenbaum
Assistant Examiner—J. L. Kruter
Attorney, Agent, or Firm—Stanley N. Garber; Andrew J. Beck; William R. O'Meara

[57] ABSTRACT

A rigid urine meter with an enclosed relatively flexible burette has a passageway at the lower end of the meter behind the burette to continuously equalize the fluid levels in the meter on either side of the burette. A groove and ribs are formed in the rear panel of the meter to support the burette, maintain its generally circular cross-section, and to provide strength and rigidity to the meter itself. The outlet port of the urine meter is directly sealed to the front panel of a drainage bag and the meter includes a lip at the port which extends into the drainage bag.

15 Claims, 8 Drawing Figures

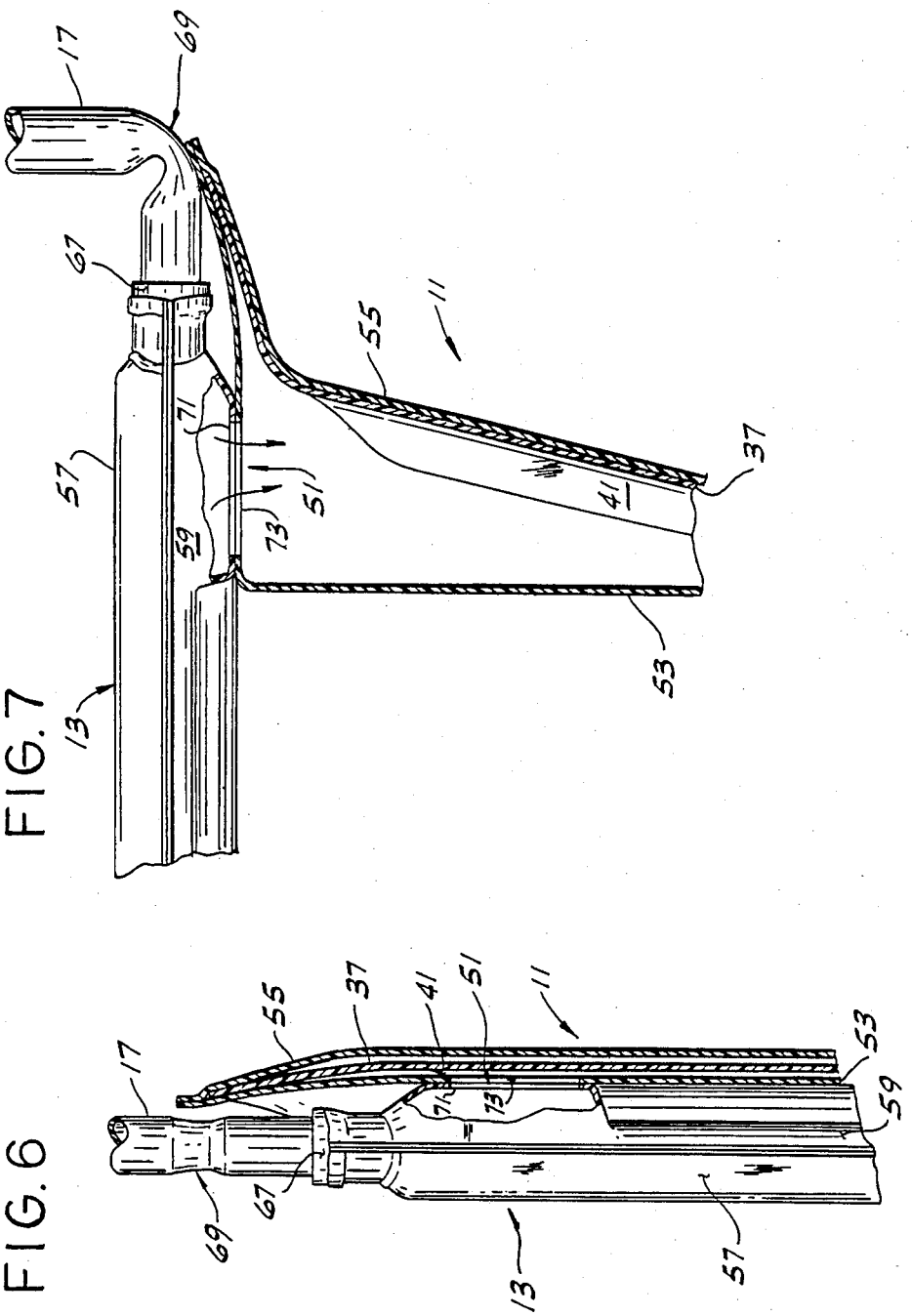

URINE METER AND DRAINAGE BAG COMBINATION

BACKGROUND OF THE INVENTION

This invention relates to urological apparatus and more specifically to urine meters with burettes and an attached drainage bag.

Urine meters in fluid communication with drainage bags such as that shown in U.S. Pat. No. Re. 30,607 are well known. Such meter bag combinations, however, require a separate part for connecting the bag to the urine meter (see FIG. 2 of the U.S. Pat. No. Re. 30,607). In urine meters it is desirable to have more accurate measurement of small volumes of urine. The U.S. Pat. No. Re. 30,607 accomplishes this by having a series of urine meter sections, each of larger volume (and less accuracy) than the preceding section. It would be desirable to have a separate chamber wholly contained inside the meter to measure these smaller volumes, but such a separate chamber cannot be formed using two vacuum-formed shells (vacuum-forming being an economical way to make such parts) if one requires the liquid level to remain the same on both sides of the meter. If a third vacuum-formed part were used to make the separate, smaller volume chamber, a second sealing opertion would be required.

It is, therefore, an object of this invention to provide a novel urine meter which can be sealed to a drainage bag without the necessity of third part between the meter and the bag; to provide a urine meter which accurately measures small volumes; to provide a urine meter with a separate chamber for measuring small volumes; and to provide such a urine meter which is reliable and economical in manufacture. Other objects and features will be in part apparent and in part pointed out hereinafter.

SUMMARY OF THE INVENTION

Briefly, the urine meter of the present invention includes a relatively rigid front panel forming the front of the meter, a relatively rigid rear panel forming the back of the meter, and a relatively flexible extruded tube extending along the axis of the meter generally from the top to the bottom thereof between the front and rear panels to form a burette. The front and rear panels are secured together along their peripheries to form the body of the meter. The tube extends from the front panel to the back panel throughout a substantial portion of its length so that the panels support the flexible tube in place. One of the panels has a passage formed therein at the bottom of the meter to permit body fluids to pass around the tube to equalize the level of such fluids in the meter on each side of the tube.

In a second aspect of the invention, the meter includes a relatively rigid front panel forming the front of the meter, a relatively rigid rear panel forming the back of the meter, and a relatively flexible tube extending generally along the axis of the meter from the top to the bottom thereof between the front and rear panels to form a burette. The front and rear panels are secured together along their peripheries to form the meter. And one of the panels has a groove in which the tube seats to prevent transverse movement of the tube.

In a third aspect of the invention, a urine meter has in combination therewith a drainage bag with which it is in fluid communication. The meter has a relatively rigid front panel forming the front of the meter and a relatively rigid rear panel forming the back of the meter. The front and rear panels are secured together along their peripheries to form the meter. The drainage bag has a relatively flexible front panel with an inlet port therein. The rear panel of the meter has an outlet port therein. And the inlet port of the front panel of the bag is directly sealed to the outlet port of the rear panel of the meter.

BRIEF DESCRIPTION OF THE DRAWINGS

FIG. 6 is a sectional view on an enlarged scale taken along lines 6—6 of FIG. 1 with the bottom portion broken away;

FIG. 7 is a view similar to FIG. 6 but showing the urine meter in its vertical position.

Similar reference characters indicate similar parts throughout the several views of the drawings.

DESCRIPTION OF THE PREFERRED EMBODIMENT

Figure 1:
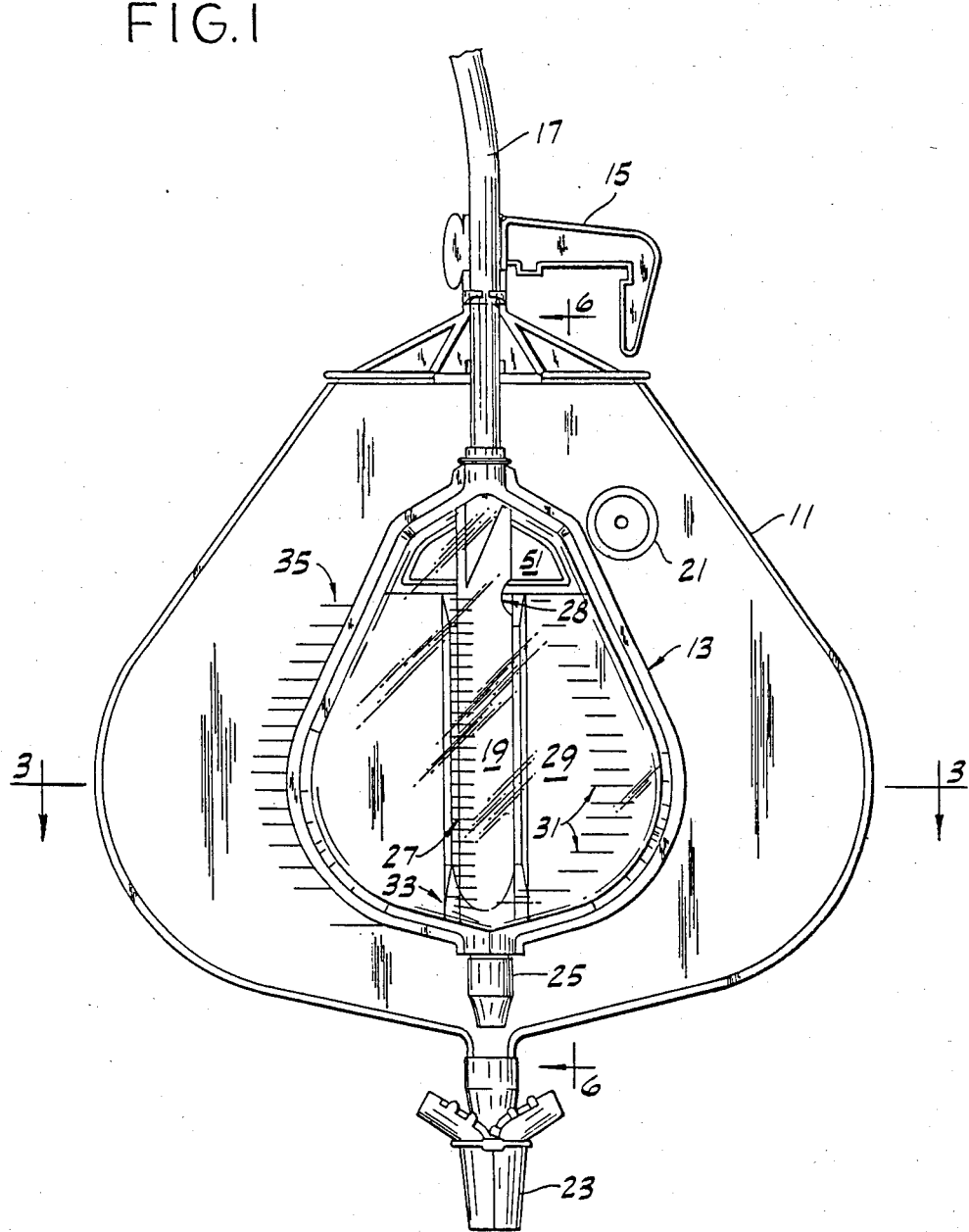
FIG. 1 is a front elevation of a urine meter and drainage bag combination of this invention.

Turning now to the drawings, there is shown in FIG. 1 a flexible urinary drainage bag 11 in combination with a relatively rigid urine metering collection chamber or urine meter 13. Bag 11 is suitably secured, by radio frequency sealing or the like, to a drainage bag support 15 such as is disclosed in co-assigned U.S. patent application Ser. No. 520,954 filed Aug. 5, 1983 so that in use bag 11 may be suspended vertically from a hospital bed or the like (not shown) to collect body fluids, e.g. urine, from a patient. Specifically, body fluid such as urine flows through a drain tube 17, which terminates at its proximal end with an inclined cut, into a burette 19 disposed inside and constituting part of meter 13. Bag 11 also has a vent 21 of conventional design secured by radio frequency sealing or the like in the front thereof to permit the expulsion of air from bag 11 as the bag is filled with urine. At the lower end of the bag 11 is a manually actuable valve 23 which when open provides a path for urine to exit from the interior of bag 11. Meter 13 similarly has a manually operable valve 25 at its lower end for the same purpose.

Figure 8:
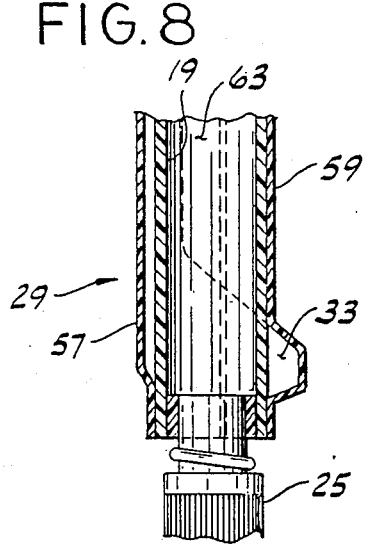
FIG. 8 is a sectional view taken along lines 8—8 of FIG. 4.

Burette 19 preferably is an extruded, relatively flexible tube of a plastic such as polyvinyl chloride (PVC). By way of example, burette 19 can have an outside diameter of about 0.75 inch (1.9 cm) and a wall of approximately 0.05 inch (1.5 mm). The burette extends from the bottom of meter 13 to generally the top thereof (approximately 6 inches (15.3 cm) for example) and is sealed at the bottom thereof to the body of the meter and valve 25 so that urine entering the burette from drain tube 17 fills burette 19 from the bottom without leaking out. Burette 19 can thus be used in conjunction with a set of gradations 27 printed or otherwise permanently affixed to the transparent vinyl (PVC) front of meter 13 to provide accurate measurement of a relatively small amount of urine, e.g. two to thirty ml. As urine fills the burette to or approaching the uppermost of gradations 27, it spills out of an opening 28 in burette 19 into the main body, labelled 29, of meter 13. Also printed or otherwise affixed on the face of meter 13 is a second set of gradations 31 which permit the measurement of somewhat larger amounts of urine, e.g. 35 to 200 ml, in the main body of the meter. As is best seen in FIG. 8, a passage 33 is provided in main body 29 behind burette 19 to ensure that urine levels in the main body of the meter on both sides of the burette are equal, so that the measurement given by gradations 31 is accurate. Because burette outlet opening 28 is on the right hand side (FIG. 1) of the burette 19 and because the bag 11 may be inadvertently tilted one way or the other during use, more urine may flow from the burette into one side of the meter than into the other side, however, the passage 33 in panel 59 will ensure that the urine levels on both sides of the burette equalize.

For convenience, the front of bag 11 is also transparent or translucent, is preferably calendared, and has printed or otherwise affixed thereon a third set of gradations 35, so that the amount of urine in the bag itself, as opposed to in the meter, may be at least approximately measured in increments of, for example, from approximately 100 ml to approximately 1800 ml.

Figure 2:
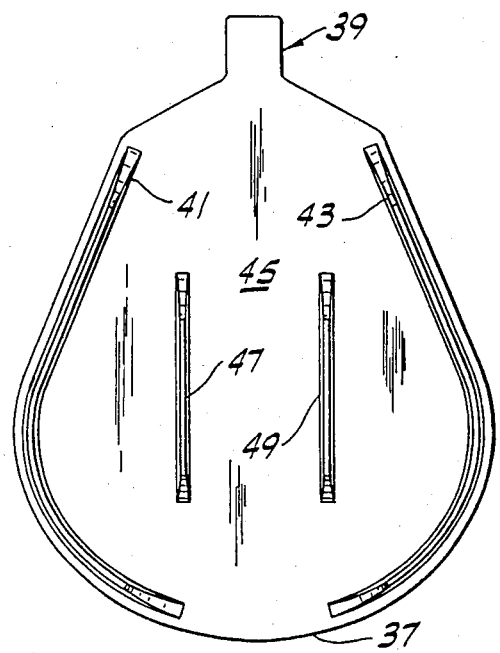
FIG. 2 is a front elevation of a spacer which is preferably disposed in the combination of FIG. 1.
Figure 4:
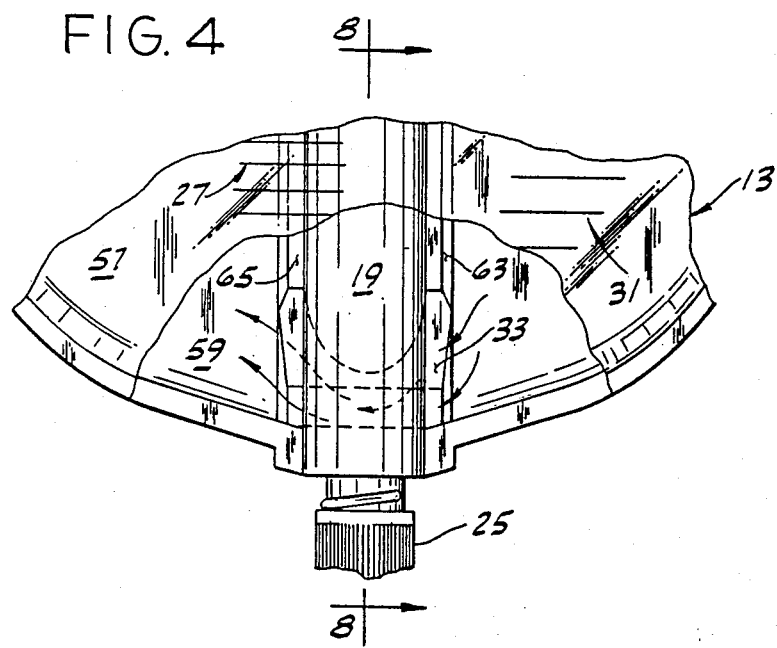
FIG. 4 is a front elevation, on an enlarged scale and with parts broken away, of the lower portion of the combination of FIG. 1.

A spacer 37 (FIG. 2) of relatively rigid polyvinyl chloride material having a thickness of approximately 0.01 inch (0.25 mm) is provided for inclusion inside bag 11. At its top spacer 37 includes a tab 39 suitable for radio frequency sealing or the like to the top of bag 11 to hold spacer 37 in place inside the bag. Along its left and right peripheries, spacer 37 includes a pair of ribs 41, 43 which extend generally perpendicularly approximately 0.5 inch (12.5 mm) out from the main body, labelled 45, of spacer 37. The size and shape of spacer 37 and the placement of ribs 41 and 43 is selected so that the urine meter seats between ribs 41 and 43. Spacer 37 also includes a second pair of ribs 47, 49 extending generally perpendicularly approximately 0.3 inch (8 mm) out from main body 45, ribs 47 and 49 being generally parallel to the longitudinal axis of spacer 37. Ribs 47 and 49 are shorter in length than ribs 41 and 43 that is, (they project out a shorter distance perpendicular to the main body of the spacer) and, as best seen in FIG. 4, terminate at their upper end in the vicinity of an inlet port or opening 51 of bag 11.

Figure 3:
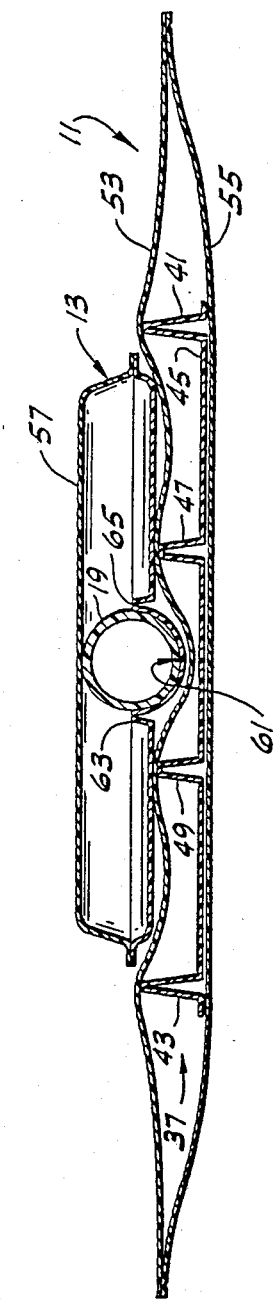
FIG. 3 is a sectional view on an enlarged scale taken along lines 3—3 of FIG. 1.

The lower portion of bag 11, meter 13, burette 19 and spacer 37 are shown in section in FIG. 3. Bag 11 is seen to have a relatively flexible, transparent front panel 53 of calendared vinyl (PVC) having a thickness of approximately 0.01 inch (0.25 mm) suitably secured as by radio frequency sealing at its periphery to a relatively flexible, opaque rear panel 55 of vinyl PVC of approximately the same thickness, said rear panel preferably being white to contrast with any urine in bag 11. Spacer 37 is disposed inside bag 11, i.e. between panels 53, 55 with ribs 41 and 43 being disposed exteriorly of meter 13. Ribs 47 and 49, on the other hand, can come into contact with the rear of meter 13 through front panel 53 of bag 11. Ribs 47 and 49 are not as tall (do not extend out from the body of spacer 37 as far) as ribs 41 and 43, thereby reducing the overall width of the bag and meter combination from what it would be if ribs 47 and 49 were as tall as ribs 41 and 43.

Meter 13 has a transparent, relatively rigid front panel 57 of vacuum formed polyvinyl chloride and opaque, preferably white, rigid rear panel 59, also of vacuum formed polyvinyl chloride, which panels are suitably sealed together such as by radio frequency sealing along their edges, each panel having a thickness of approximately 0.025 inch (0.6 mm). Rear panel 59 has formed therein a recess or groove 61 and a pair of ribs 63, 65 to receive and support flexible burette tube 19 against transverse movement. The ribs also strengthen the meter itself and maintain the circular cross-section of the burette. Ribs 63 and 65 terminate short of the bottom of meter 13 (see FIG. 4) and channel 33 is formed in rear panel 59 (see FIG. 8) to permit urine to freely flow behind burette 19 to equalize the urine levels in each half of meter 13. Referring back to FIG. 3, front panel 57 supports burette 19 as well by being in frictional contact therewith even though the front panel is not molded to receive the burette.

Figure 5:
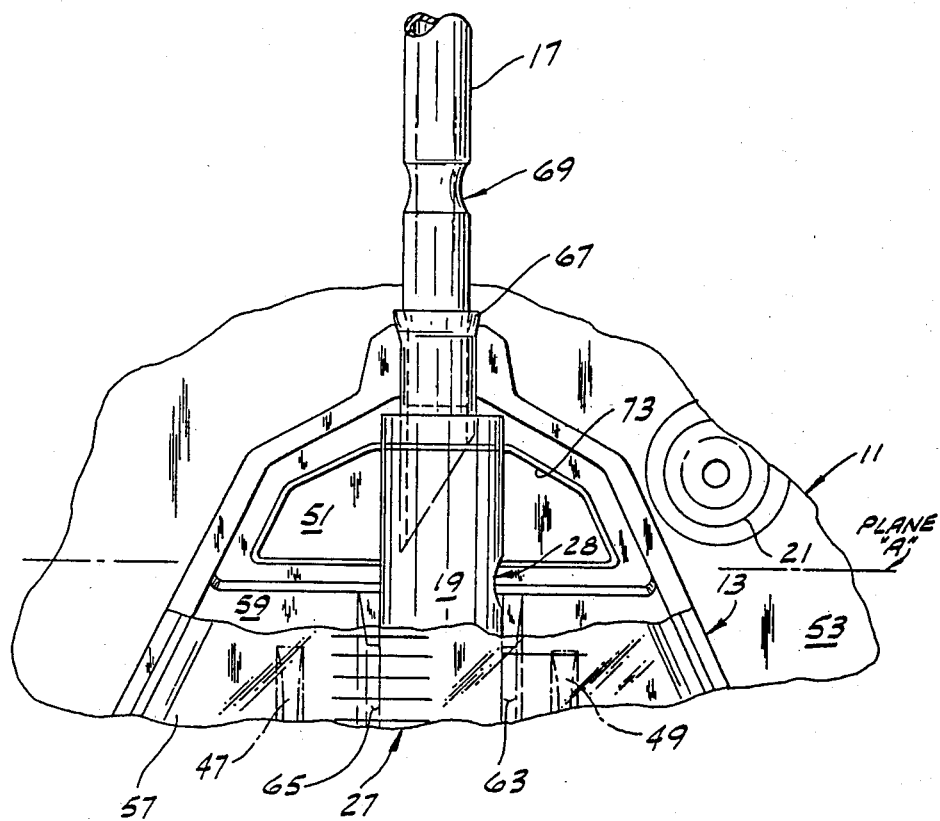
FIG. 5 is a front elevation, on an enlarged scale and with parts broken away, of the upper portion of the combination of FIG. 1.

The tops of meter 13 and burette 19 are shown in greater detail in FIG. 5. Drain tube 17 is secured in the top of meter 13 in a clear plastic bushing 67 of PVC whose inclined lower end terminates in burette 19 and which is itself secured by a suitable adhesive or sealing process to the top of meter 13. Rigid panels 57 and 59 extend around bushing 67 and help hold it in place. The inclined proximal end of bushing 67 thus constitutes the inlet port of meter 13. Tube 17 extends generally from the inlet port of meter 13 upwardly a predetermined distance to a section thereof labelled 69 which has a length much shorter than the predetermined distance. At section 69 the wall of tube 17 has been thinned to provide a predetermined point of weakness. This thinning, which is exaggerated in FIGS. 5–7, is accomplished without changing the inner diamter of tube 17, which diameter remains substantially constant throughout its length by, for example, placing the proximal portion of the tube over a mandrel and rotating it about its longitudinal axis while simultaneously heating section 69 and stretching the tube. By way of example, the inner diameter of tube 17 throughout its length is approximately 0.3 inch (8 mm) while the outer diameter can vary from 0.4 inch (1 cm) above and below section 69 to approximately 0.36 inch (9 mm) at section 69. However, even this much thinning of the wall is not necessary. All that is required is that the wall be thinned enough at section 69 to make section 69 the weakest part of the tube 17 so that when bent, the tube will kink off at that point.

The purpose of section 69 is illustrated in FIGS. 6 and 7. Rear panel 59 of urine meter 13 has an outlet port 71 molded therein with a lip 73 thereof which extends into and is suitably secured to front panel 53 of bag 11. As urine fills meter 13 to the bottom of outlet port 71, the urine spills over lip 73 through inlet port 51 of bag 11 into the bag. Many times, however, the meter is not allowed to become this full. Rather, periodically a nurse records the amount of urine in meter 13 and then rotates meter 13 from its generally vertical portion of FIG. 6 around plane A (FIG. 5) to a substantially horizontal position shown in FIG. 7 to dump the contents of the meter into the bag. Section 69, being the point of weakness, thereupon kinks off tube 17. This action closes the lumen of tube 17 and ensures that the urine passes into bag 11 instead of traveling up tube 17.

When the urine is dumped into bag 11, spacer 39 and specifically ribs 41, 43, 47 and 49 hold walls 53 and 55 of the bag apart to promote rapid dumping of the urine into the bag. The calendared texture of front panel 53 also promotes rapid dumping as it reduces the tending of the front and rear panels of the bag to stick together.

In view of the above it will be seen that the objects of the invention are achieved and other advantageous results attained.

Although the invention has been described with reference to the preferred embodiment illustrated in the drawings, many modifications will be apparent to those skilled in the art without departing from the spirit or scope of this invention.

What is claimed is:

1. A meter for collecting and measuring body fluids comprising a relatively rigid front panel forming the front of the meter, said meter having a longitudinal axis, a relatively rigid rear panel forming the back of the meter, the front and rear panels being secured together along their peripheries to form the meter, and a relatively flexible tube extending along said axis of the meter substantially from the top to the bottom thereof between the front and rear panels to form a burette to receive body fluid from a patient, said burette extending substantially from the front panel to the back panel throughout a substantial portion of its length, the burette being supported in place by the front and rear panels and having an outlet in fluid communication with the meter, one of said panels having a passage means formed therein within and at the bottom of the meter extending transversely of the burette and said axis and in fluid communication with portions of the meter on both sides of the burette to permit body fluids to pass transversely by the burette to equalize the level of fluids in the portions of the meter on each side of the burette when the meter is in use.

2. The meter as set forth in claim 1 wherein the passage means is formed in the rear panel.

3. The meter as set forth in claim 2 wherein the rear panel is generally planar and the passage means formed in the rear panel extends out of the plane of the rear panel.

4. The meter as set forth in claim 1 in which one of said panels includes a groove in which the burette seats to prevent transverse movement of the burette.

5. The meter as set forth in claim 4 wherein the panel with the groove further includes a pair of ribs, one on each side of the groove and parallel thereto, to further support the burette.

6. The meter as set forth in claim 5 wherein the groove and ribs are formed in the same panel as the passage and terminate above said passage means.

7. A meter for collecting and measuring body fluids comprising a relatively rigid front panel forming the front of the meter, a relatively rigid rear panel forming the back of the meter, said meter having a vertical longitudinal axis, the front and rear panels being secured together along their peripheries to form the meter, and a relatively flexible tube extending substantially along said vertical axis of the meter from the top to the bottom thereof between the front and rear panels to form a burette, means closing the bottom of said burette to allow the burette to collect body fluid therein, one of said panels having a groove extending along said axis and in which the burette seats to prevent movement of the burette transversely of said axis, and drain tube means having one end portion for connection with a source of body fluid and the opposite end portion extending into the meter in fluid tight sealing engagement therewith and also extending into the burette for conveying body fluid thereto, the burette having an outlet adjacent the upper end thereof in fluid communication with the meter so that body fluid can flow from the burette into the meter, and transverse passage means in fluid communication with the meter on both lateral sides of the burette at the bottom of the meter to allow body fluid to flow laterally by the burette to equalize levels of body fluid on the lateral sides of the burette.

8. The meter as set forth in claim 7 wherein the panel with the groove further includes a pair of ribs, one on each side of the groove and parallel thereto, to further support the tube.

9. A meter for collecting and measuring body fluids comprising a relatively rigid front panel forming the front of the meter, a relatively rigid rear panel forming the back of the meter, the front and rear panels being secured together along their peripheries to form the meter, and a relatively flexible tube extending generally along the axis of the meter from the top to the bottom thereof between the front and rear panels to form a burette, one of said panels having a groove in which the tube seats to prevent transverse movement of the tube, the panel with the groove further including a pair of ribs, one one each side of the groove and parallel thereto, to further support the tube, the groove and ribs being formed in the rear panel, and the front panel being comparatively flat.

10. In combination, a meter for collecting and measuring body fluids and a drainage bag in fluid communication therewith, said meter having a relatively rigid front panel forming the front of the meter and a relatively rigid rear panel forming the back of the meter, the front and rear panels being secured together along their peripheries to form the meter, said drainage bag having a relatively flexible front panel with an inlet port therein, the rear panel of the meter having an outlet port therein, the inlet port of the front panel of the bag being directly sealed to the outlet port of the rear panel of the meter, the meter including a relatively flexible extruded tube extending along the axis of the meter generally from the top to the bottom thereof between the front and rear panels of the meter to form a burette, the tube extending substantially from the front panel to the back panel of the meter throughout a substantial portion of its length, the flexible tube being supported in place by the front and rear meter panels, one. of said meter panels having a passage formed therein at the bottom of the meter extending generally transversely of said axis to permit body fluids to pass around the tube to equalize the level of such fluids in the meter on each side of the tube.

11. The combination as set forth in claim 10 wherein one of the panels includes a groove in which the tube seats to prevent transverse movement of the tube.

12. The combination as set forth in claim 11 wherein the panel with the groove further includes a pair of ribs, one on each side of the groove and parallel thereto, to further support the tube.

13. A urine meter for collecting and measuring urine comprising a relatively rigid front panel forming the front of the meter, a relatively rigid rear panel forming the back of the meter, the front and rear panels being secured together along their peripheries to form a meter chamber, and a relatively flexible tube having an upper end and a lower end extending substantially vertically and generally from the top to the bottom thereof and between and closely adjacent the front and rear panels to form a burette substantially dividing the meter chamber into laterally spaced chamber portions, means including a drain tube for introducing urine into the burette, the burette having an outlet adjacent the upper end thereof so that urine is flowable from the burette to said chamber portions, the lower end of said burette being fixedly connected to the meter at the bottom thereof, one of said panels having a transverse passage formed therein at the bottom of the meter chamber extending generally laterally between said chamber portions connecting said chamber portions together in fluid communication to permit urine to pass laterally by the burette between said chamber portions to equalize the level of urine in said chamber portions during use of the meter.

14. The meter of claim 13 wherein said burette is circular in cross-section.

15. The meter of claim 14, wherein one of said panels has a vertically extending groove within the meter receiving portions of the burette to prevent lateral movement of upper portions of the burette.

* * * * *